United States Patent [19]

Takeuchi et al.

[11] Patent Number: 6,075,135
[45] Date of Patent: Jun. 13, 2000

[54] 3,4-DI-O,N-PROTECTED-4-AMINO-2,4,6-TRIDEOXY-2-FLUORO-L-MANNO-PYRANOSYL HALIDE AND A PROCESS FOR ITS PREPARATION

[75] Inventors: Tomio Takeuchi; Sumio Umezawa, both of Tokyo; Tsutomu Tsuchiya; Yasushi Takagi, both of Yokohama, all of Japan

[73] Assignee: Zaidan Hojin Biseibutsu Kagaku Kenkyu Kai, Tokyo, Japan

[21] Appl. No.: 09/282,200

[22] Filed: Mar. 31, 1999

Related U.S. Application Data

[62] Division of application No. 08/981,255, filed as application No. PCT/JP96/01697, Jun. 19, 1996, Pat. No. 5,958,889.

[30] Foreign Application Priority Data

Jun. 23, 1995 [JP] Japan .................................. 7-179621

[51] Int. Cl.⁷ .................. C07H 1/00; C07H 5/00
[52] U.S. Cl. ..................... 536/17.5; 536/4.1; 536/6.4; 536/17.2; 536/18.5; 536/18.7; 536/124
[58] Field of Search ............. 536/4.1, 6.4, 18.5, 536/18.7, 17.2, 17.5, 124

[56] References Cited

U.S. PATENT DOCUMENTS 5,034,517  7/1991  Umezawa et al. ..................... 536/18.5

*Primary Examiner*—Elli Peselev
*Attorney, Agent, or Firm*—Larson & Taylor LLP

[57] ABSTRACT

7-O-(4-Amino-2,4,6-trideoxy-2-fluoro-α-L-mannopyranosyl)-daunomycinone or -adriamycinone is now synthesized as a daunomycinone or adriamycinone derivative having the general formula

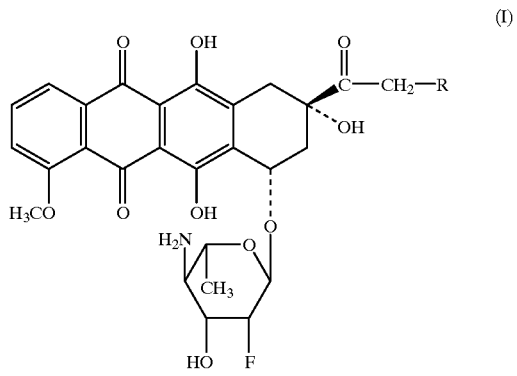

(I)

wherein R is a hydrogen atom or hydroxyl group. These novel compounds according to this invention exhibit excellent antitumor activities and have a high solubility in water, and hence they are useful as an antitumor agent.

3 Claims, No Drawings

3,4-DI-O,N-PROTECTED-4-AMINO-2,4,6-TRIDEOXY-2-FLUORO-L-MANNO-PYRANOSYL HALIDE AND A PROCESS FOR ITS PREPARATION

This is a division of application Ser. No. 08/981,255 filed Dec. 22, 1997, now U.S. Pat. No. 5,958,889; which is a 371 of PCT/JP96/01697 filed Jun. 19, 1996.

TECHNICAL FIELD

This invention relates to novel anthracycline derivatives which exhibit an excellent anticancer or antitumor activity at a low dosage thereof and which have 4-amino-2,4,6-trideoxy-2-fluoro-α-L-mannopyranosyl group as the sugar moiety. This invention also relates to processes for the preparation of said novel anthracycline derivatives and further to a pharmaceutical composition comprising the same as an active ingredient. More particularly, this invention relates to 7-O-(4-amino-2,4,6-trideoxy-2-fluoro-α-L-mannopyranosyl)daunomycinone and 7-O-(4-amino-2,4,6-trideoxy-2-fluoro-α-L-mannopyranosyl)adriamycinone or their acid addition salts as the novel anthracycline derivatives having an anticancer or antitumor activity and a low toxicity. This invention also relates to a pharmaceutical composition containing the novel anthyracycline derivative or an acid addition salt thereof. Further, this invention relates to processes for the preparation of these novel anthracycline derivatives. Yet further, this invention relates to a novel compound useful as an intermediate for the synthesis of these novel anthracycline derivatives.

BACKGROUND ART OF INVENTION

As antibiotics of the anthracycline type are known daunomycin which is also named daunorubicin in the specification of U.S. Pat. No. 3,616,242, as well as adriamycin which is also named doxorubicin in the specification of U.S. Pat. No. 3,590,028. These compounds have broad anticancer spectra against experimental tumors and have widely been utilized for clinical purposes as a chemotherapeutic anticancer agent.

While, daunomycin and adriamycin can exhibit a somewhat strong anticancer or antitumor activity against various kinds of cancers or tumors, but are not necessarily satisfactory as the anticancer agent or antitumor agent. That is, daunomycin and adriamycin have been utitlized widely as a chemotherapeutic anticancer agent for clinical treatment of cancer-bearing patients, but they are also known to bring about serious side-effects such as leukocytopenia, alopecia, myocardiopathy and others, in many instances.

Therefore, it has hitherto been attempted to produce newly a variety of novel daunomycin-related compounds with the intention of providing such novel daunomycin-related compounds which would have a much enhanced anticancer or antitumor activity but with exhibiting a low toxicity. As some outcome of the attempts hitherto made, there have been proposed several compounds, for example, those known as aclacinomycins A and B; 4'-O-tetrahydropyranyl-adriamycin; N-monobenzyl- or N-dibenzyl-adriamycin.

Besides, U.S. Pat. No. 4,427,664 specification discloses 7-O-(3,4-di-O-acetyl-2,6-dideoxy-2-iodo-α-L-manno-hexopyranosyl)daunomycinone and 7-O-(3,4-di-O-acetyl-2,6-dideoxy-2-iodo-α-L-talo-hexopyranosyl)daunomycinone.

We, the present inventors, proceeded with our investigations in an attempt to provide novel derivatives of daunomycin and adriamycin which will exhibit a higher anticancer or antitumor activity than those of daunomycin or adriamycin but with a low toxicity. As a part of our investigations, we have already synthesized some derivatives of daunomycin and adriamycin in which the sugar moiety of daunomycin and adriamycin has been chemically modified. For example, the present inventors already reported 4'-O-tetrahydropyranyl-daunomycin or -adriamycin as well as 3'-deamino-3'-morpholino-daunomycin or -adriamycin.

Further, the present inventors succeeded in synthesizing such anthracycline derivatives having antitumor activities which are represented by the following general formula (A)

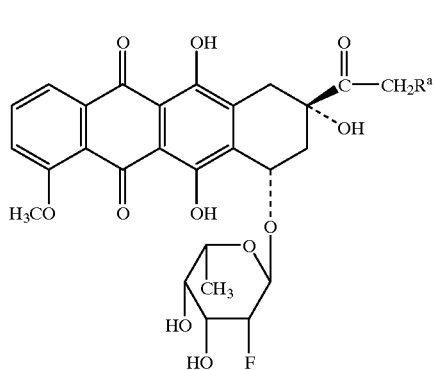

(A)

wherein $R^a$ stands for a hydrogen atom or a hydroxyl group, that is, 7-O-(2,6-dideoxy-2-fluoro-α-L-talopyranosyl)daunomycinone and 7-O-(2,6-dideoxy-2-fluoro-α-L-talopyranosyl)adriamycinone, which possess an anticancer or antitumor activity (see Japanese Patent Publication "Kokoku" Hei 6-31298 and European Pat. No. 0230013).

The present inventors also succeeded in synthesizing such anthracycline derivatives having antitumor activities which are represented by the following general formula (B)

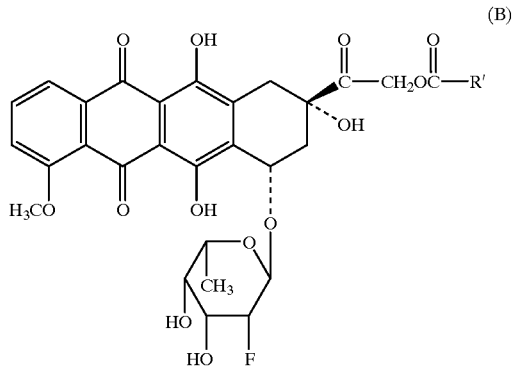

(B)

wherein R' stands for a group —$(CH_2)_m$—H where m is an integer of 1~6, or R' stands for a group —$(CH_2)_n$—COOH where n is an integer of 1~10 (see Japanese Patent Publication "Kokoku" Hei 7-42304 and European Patent No. 0275431).

The present inventors further succeeded in synthesizing such anthracycline derivatives having antitumor activities which are represented by the following general formula

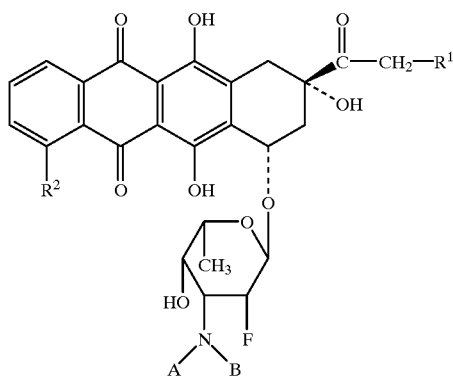

(C)

wherein $R^1$ is a hydrogen atom or a hydroxyl group, $R^2$ is a methoxy group or a hydrogen atom, and A and B each stand for a hydrogen atom or A and B as taken together form a chain of formula —$CH_2$—$CH_2$—O—$CH_2$—$CH_2$— (see Japanese Patent Application First Publication "Kokai" Sho-64-203397). As examples of the anthracycline derivatives of the general formula (C), there may be mentioned 7-O-(3-amino-2,3,6-trideoxy-2-fluoro-α-L-talopyranosyl) daunomycinone; 7-O-(3-amino-2,3,6-trideoxy-2-fluoro-α-L-talopyranosyl)adriamycinone; 7-O-(2,3,6-trideoxy-2-fluoro-3-morpholino-α-L-talopyranosyl)adriamycinone and others.

7-O-(2,6-Dideoxy-2-fluoro-α-L-talopyranosyl) adriamycinone, as one of the anthracycline derivatives of the general formula (A) given above, exhibits a remarkable antitumor activity, but is barely soluble in water, so that it had a difficulty in formulating it into injection preparations. Then, the anthracycline derivatives of the general formulae (B) and (C) above have been synthesized in an attempt to give such anthracycline derivatives which have an improved solubility in water. Amongst the derivatives of the general formula (C), 7-O-(3-amino-2,3,6-trideoxy-2-fluoro-α-L-talopyranosyl)adriamycinone is soluble in water, but the antitumor activity thereof has not been recognized to be remarkably higher than that of adriamycine, even though the former has the antitumor activity a little higher than that of the latter.

The present inventors further have continued our investigations in various ways with the intention of producing such novel anthracycline derivatives which can exhibit higher anticancer or antitumor activities than those of daunomycin, adriamycin and the antitumor anthracycline derivatives of the general formulae (A), (B) and (C) above, even at a low dosage, and which are of satisfactory solubility in water and of low toxicity.

The anticancer or antitumor activities of the anthracycline derivatives of the general formulae (A) and (B) above are, in fact, noticeably superior to those of daunomycin and adriamycin, but are not yet satisfactorily high enough. All of the anthracycline derivatives of the general formula (C) above are soluble in water, but most of those derivatives exhibit only an anticancer or anti-tumor activity substantially as high as or lower than that of adriamycin.

Therefore, there still exists a desire for providing such novel anthracycline derivatives which can exhibit higher anticancer or antitumor activities than those of the known anthracycline derivatives. Further, in general, it is always convenient for clinical applications to administer the anticancer or antitumor compounds in the form of injectable preparations. Thus, for the purpose of therapeutic treatments of a variety of cancers and tumors, a demand always exists in the art to provide and explore such novel anticancer or antitumor agents having a nature that they can exhibit a strong anticancer or antitumor activity but with low toxicity and also they are highly soluble in water.

DISCLOSURE OF INVENTION

In order to solve the problems above-mentioned, the present inventors have proceeded with our further investigations in an attempt to synthesize novel anthracycline derivatives having a new fluorinated amino-sugar moiety.

As a result of these further investigations, we have now succeeded in synthesizing 1-O-acetyl derivative of 4-amino-2,4,6-trideoxy-2-fluoro-α-L-mannopyranose and 4-amino-2,4,6-trideoxy-2-fluoro-α-L-mannopyranosyl bromide or their 3,4-di-O,N-protected derivatives as new compounds through a multi-step method with starting from methyl 4-O-benzyl-2,6-dideoxy-2-fluoro-α-L-talopyranoside which has been obtained in the synthesis of the anthracycline derivative of the general formula (A) shown hereinbefore.

Then, by utilizing these 4-amino-2,4,6-trideoxy-2-fluoro-α-L-mannopyranose derivatives as synthesized for the first time and by taking such a method which comprises condensing the 4-amino-2,4,6-trideoxy-2-fluoro-α-L-mannopyranosyl group with the 7-hydroxyl group of daunomycinone or adriamycinone, we have now succeeded in synthesizing such novel daunomycinone derivative or adriamycinone derivative which is represented by a general formula (I) described hereinafter, or an acid addition salt thereof, as such new anthracycline derivatives which bear a 4-amino-2,4,6-trideoxy-2-fluoro-α-L-mannopyranosyl group as the sugar moiety. Furthermore, we have found that the novel anthracycline derivatives of the general formula (I) are soluble in water, that they exhibit a high anticancer or antitumor activity even when they are administered to test animals at low dosages, and that development of acute toxicity does not take place in the test animals having received the administration of the anthracycline derivative of the formula (I) at the low dosages which can give high anticancer or antitumor effects in the test animals so treated.

In a first aspect of this invention, therefore, there is provided a daunomycinone or adriamycinone derivative represented by the following general formula

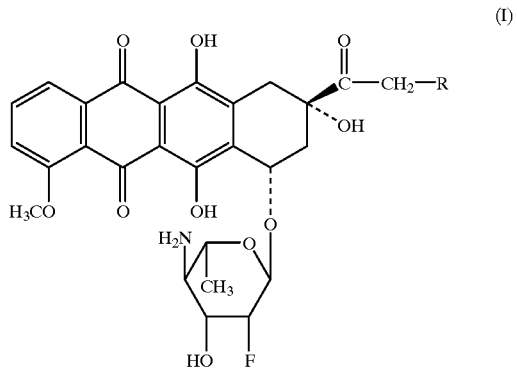

(I)

wherein R is a hydrogen atom or a hydroxyl group, or a pharmaceutically acceptable acid addition salt thereof.

As examples of the pharmaceutically acceptable acid addition salts of the daunomycinone or adriamycinone derivative of the general formula (I), there are mentioned such acid addition salts which may be formed by reacting the 4'-amino group of said derivative with a pharmaceutically acceptable inorganic acid such as hydrochloric acid, sulfuric acid and phosphoric acid, or a pharmaceutically acceptable organic acid such as acetic acid, propionic acid, citric acid, lactic acid, methanesulfonic acid in a usual manner.

Examples of the daunomycinone or adriamycinone derivative of the general formula (I) include Compound (a) and Compound (b) of this invention indicated below.

(1) Compound (a)

7-O-(4-amino-2,4,6-trideoxy-2-fluoro-α-L-mannopyranosyl)daunomycinone having the following formula

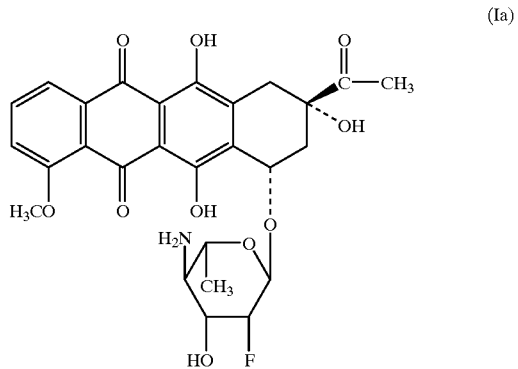

(Ia)

(see Example 1 given hereinafter).

(2) Compound (b)

7-O-(4-amino-2,4,6-trideoxy-2-fluoro-α-L-mannopyranosyl)adriamycinone having the following formula

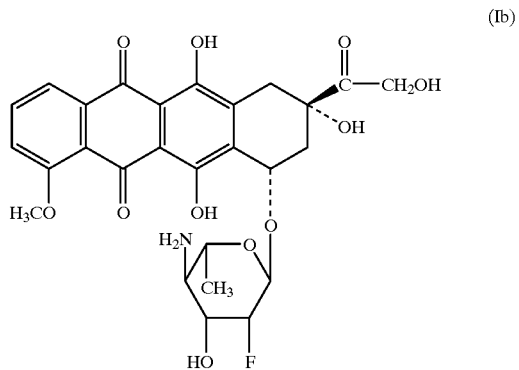

(Ib)

(see Example 2 given hereinafter).

It has been confirmed through "in vivo" tests that the novel anthracycline derivatives of the general formula (I) exhibit a remarkably high antitumor activity against experimental tumors in animals and has an antitumor activity substantially as hig as or remarkably improved over daunomycin and adriamycin when the compound of the formula (I) is administered at low dosages.

Now, some Test examples are given to illustrate the antitumor activities of Compound of the formula (Ia) and Compound of the formula (Ib) shown above, which are embraced by the anthracycline derivatives of the general formula (I) according to the first aspect of this invention.

Test Example 1

In this Example, some tests were made to demonstrate antitumor activities of the compounds of this invention shown against leukemia in $CDF_1$ mice as induced by a mouse leukemia, Leukemia L-1210 cells.

Thus, to evaluate the antitumor effects of the novel compounds of this invention against experimental tumors in animals, $CDF_1$ mice (four mice per group) were intraperitoneally inoculated with cells of Leukemia L-1210 at an amount of $1 \times 10^5$ cells/mouse. Since an elapse of 24 hours from the inoculation of the leukemia cells, a test compound of this invention was administered intraperitoneally to the mice under test once a day for consecutive 9 days, with the test compound being given as its hydrochloride in the form of a solution in a physiological saline. The mice so treated were observed for 60 days after the administration of the test compound. In the meanwhile, mice of the control group (the untreated group) were administered only with physiological saline after the inoculation of the L-1210 cells. During the observation period, the number of the surviving mice was counted for both the treated group and the control group, and the mean survival days of mice of both the treated group and the control group were calculated. Then, the percentages (%) of increase in the life-span of the treated mice was estimated, as T/C (%), in terms of the mean survival day (C) of the untreated mice of the control group and the mean survival day (T) of the treated mice of the treated group. For comparison purposes, similar tests were effected using 7-O-(3-amino-2,3,6-trideoxy-2-fluoro-α-L-talopyranosyl)adriamycinone (abbreviation: 3-A-FT-ADM) (as hydrochloride), daunomycin (as hydrochloride) and adriamycin (as hydrochloride). The test results are shown in Table 1 below. The mean survival day of mice of the control group (the untreated group) was 8 to 9 days, and the mean survival day of mice of the comparative groups having received the administration of daunomycin or adriamycin usually varied dependently on the dosage of daunomycin or adriamycin tested.

In Table 1 below, the symbol ">" indicates that, among the four mice under test which were inoculated with the tumor cells and then administered with the compound under test, there existed at least one mouse which could be cured and survived for 60 days or longer by the administration of the test compound in spite of their received inoculation of tumor cell. Incidentally, in respect of the fractional numbers parenthesized below the numerical values of increase (%) in the life-span, the denominator of the fraction denotes the number of mice tested in one test group but the numerator of the fraction denotes the number of mice which survived for 60 days or longer.

TABLE 1

| | Increase (%) in life-span (T/C, %) Dosage (mg/kg/day) | | | | | |
|---|---|---|---|---|---|---|
| Compound tested | 5 | 2.5 | 1.25 | 0.6 | 0.3 | 0.15 |
| 7-O-(4-amino-2,4,6-trideoxy-2-fluoro-α-L-mannopyranosyl)daunomycinone [Compound (a) of this invention] (as hydrochloride) | 98* | 115* | 141* | 157 | 141 | 138 |
| 7-O-(4-amino-2,4,6-trideoxy-2-fluoro-α-L-mannopyranosyl)adriamycinone [Compound (b) of this invention] (as hydrochloride) | 138* | 193* | >787 (4/4) | >561 (2/4) | >544 (2/4) | 200 |

TABLE 1-continued

| | Increase (%) in life-span (T/C, %) Dosage (mg/kg/day) | | | | | |
|---|---|---|---|---|---|---|
| Compound tested | 5 | 2.5 | 1.25 | 0.6 | 0.3 | 0.15 |
| 7-O-(3-amino-2,3-6-trideoxy-2-fluoro-α-L-talopyranosyl)adriamycinone (3-A-FT-ADM) (as hydrochloride) (Comparative) | 97* | 187* | 168* | 203 | 135 | 123 |
| Daunomycin (as hydrochloride) (Comparative) | 138* | 171* | 158 | 145 | 112 | 132 |
| Adriamycin (as hydrochloride) (Comparative) | 177* | 273* | 330 | 208 | 132 | 140 |

Notes:
Asterisks (*) indicate that development of toxicity such as toxicity-related death or a body weight loss was observed on the corresponding mice tested.

In the "in vivo" tests as described above, all the compounds of the general formula (I) according to the first aspect of this invention are soluble in water and exhibit high antitumor activities. In these tests, the daunomycinone derivative of the general formula (I) according to this invention, namely Compound (a) of this invention as given at a dosage in a range of 0.6~1.25 mg/kg was able to exhibit antitumor activities substantially as high as those of daunomycin but exhibited antitumor activities inferior to those of the comparative 3-A-FT-ADM. On the other hand, it is found that Compound (b) of this invention, namely the adriamycin derivative as given at a low dosage in a range of 1.25~0.3 mg/kg was able to exhibit such remarkably high antitumor activities that the percentage of the increase in the life-span (T/C, %) was as high as a value of greater than 544% to a value of greater than 787%, and that the number of the mice surviving for 60 days (the mice as fully cured from the leukemia) amounted to eight in twelve. This indicates that Compound (b) given at a dosage of 1.25~0.3 mg/kg was able to exhibit markedly enhanced anticancer or antitumor activities, as compared with those of adriamycin as given at a dosage of 1.25~0.3 mg/kg. Furthermore, it is found that Compound (b) of this invention as given at a low dosage of 1.25~0.3 mg/kg was able to exhibit remarkably enhanced anticancer or antitumor activities in terms of the percentages of increase in the life-span of the treated mice (T/C, %), in comparison with 3-A-FT-DDM.

Daunomycin or adriamycin used as the comparative drug in the above Test Example 1 is an anticancer agent which has been used clinically and practically administered to human beings at a dosage in the range of 0.4 mg/kg~2 mg/kg in dependent upon the nature of cancers to be treated. When daunomycin or adriamycin is administered at a dosage ranging from 2.5 mg/kg/day to 5 mg/kg/day to such mice as inoculated with the L-1210 cancer cells, daunomycin or adriamycin exhibits an anticancer or antitumor activities which amount to the percentages of increase in the life-span (T/C, %) of 138%~171% or of about 330% at maximum, respectively, with being accompanied by the development of toxicity.

It is to be noticed that, in contrast to daunomycin or adriamycin, the adriamycinone derivative of the formula (Ib), namely Compound (b) of this invention, when administered at a proper low dosage in the range of 0.3 ~1.25 mg/kg/day to the mice as inoculated with the L-1210 cancer cells, is able to exhibit such extremely excellent anti-tumor effects that the development of toxicities is not involved, while the attainable values of the percentages of increase in the life-span (T/C, %) are markedly higher than those attainable by daunomycin or adriamycin, and that particularly, the percentages of increase in the life-span can amount to about 550% or higher with involving a complete cure. Accordingly, Compounds (a) and (b) of this invention, particularly Compound (b), have such advantage that significant antitumor effects can be expected to be attained by them even when they are administered at a not too high dosage to the cancer-bearing patients for clinical treatments.

Judging from the foregoing, it is expected that the novel anthracycline derivatives of the general formula (I) according to the first aspect of this invention, owing to their excellent antitumor activities and their high water-solubility, are very much useful as the antitumor agents to be used for clinical treatments, and that they are utilizable for therapeutic treatments of a variety of tumors, similarly to daunomycin or adriamycin. Accordingly, the compounds of the general formula (I) according to this invention can be used usefully as a therapeutic agent for tumors or cancers in the therapeutic treatments of solid cancers, ascitic cancers and the like.

According to a second aspect of this invention, therefore, there is provided a pharmaceutical composition, particularly an antitumor composition, characterized in that it comprises as an active ingredient a daunomycinone or adriamycinone derivative of the general formula (I) defined hereinbefore or a pharmaceutically acceptable acid addition salt thereof, in combination with a pharmaceutically acceptable carrier.

When the compound of the general formula (I) according to this invention is administered in practice, it may usually be administered also parenterally. It is also feasible to administer the compound of this invention orally after the compound is mixed with a pharmaceutically acceptable solid or liquid carrier which is used conventionally in the pharmaceutic field, followed by formulating the resulting mixture into various preparation forms such as powder, granules, tablets or syrups, or injections.

As a general method for the administration, the compound of this invention may be administered to animals in the form of an injectable preparation by intraperitoneal injection, subcutaneous injection, intravascular injection, either intravenous or intra-arterial, or local injection, and the like. For the administration to human beings, the compound of this invention may be administered in the form of an injectable preparation by intravascular injection, either intravenous or intra-arterial, or local injection, and the like. The compound of this invention may be administered consecutively or intermittently at such dosage and to such extent that the total dosage of the compound given would not exceed a certain level as determined in view of results of preliminary animal tests and various circumstances.

Of course, however, the administration of the compound of this invention should be carried out with changing the dosage of the compound appropriately in accordance with the way of administration and the conditions of the patients or animals to be treated, for example, age, body weight, sex, sensitivity, foods, administration time, administration route, drug(s) to be concurrently administered, and the seriousness of patients or their disease and others. The compound of this invention may be administered at a substantially same dose as or at a lower dose than that of daunomycin or adriamycin when the compound is given as an antitumor or anticancer agent. Optimum dosage and frequency of administration of the compound of this invention under certain specific conditions must be determined by medical experts through preliminary tests in view of the above-mentioned guidelines.

These requirements for administration are similarly applied to the oral administration of the compound of this invention.

Now, processes for the preparation of the daunomycinone derivative or adriamycinone derivative of the general formula (I) according to the first aspect of this invention will be described below.

For the preparation of 7-O-(4-amino-2,4,6-trideoxy-2-fluoro-α-L-mannopyranosyl)-daunomycinone or -adriamycinone represented by the general formula (I), it is necessary to use 1-O-acetyl derivative of a 3-O-protected-4-N-protected-4-amino-2,4,6-trideoxy-2-fluoro-α-L-mannopyranose or a 3-O-protected-4-N-protected-4-amino-2,4,6-trideoxy-2-fluoro-α-L-mannopyranosyl bromide or iodide which are each a new sugar compound. The respective steps (1)~(8) which are effected in the synthesis of these new sugar compounds are firstly explained below in brief. Referential Example 1 given hereinafter will describe in details the reactions which are involved in these respective steps of said synthetic process.

In the following descriptions, abbreviation Bn means benzyl group, and abbreviation Ac means acetyl group. And, abbreviation TBS means tertiary-butyldimethylsilyl group [—Si(CH$_3$)$_2$—C(CH$_3$)$_3$].

Step (1)

A known compound, methyl 4-O-benzyl-2,6-dideoxy-2-fluoro-α-L-talopyranoside [Compound (1)] of the following formula

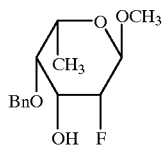

is reacted with tert-butylchlorodimethylsilane [(CH$_3$)$_3$CSi—(CH$_3$)$_2$Cl] to silylate the 3-hydroxyl group of Compound (1) and to give methyl 4-O-benzyl-3-O-tert-butyldimethylsilyl-2,6-dideoxy-2-fluoro-α-L-talopyranoside [Compound (2)] having the following formula

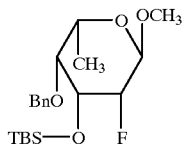

as the 3-O-silyl derivative.

Step (2)

The benzyl group at the 4-position of Compound (2) is eliminated therefrom by catalytic reduction with hydrogen in the presence of a palladium catalyst, to produce methyl 3-O-tert-butyldimethylsilyl-2,6-dideoxy-2-fluoro-α-L-talopyranoside [Compound (3)] of the following formula

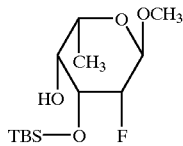

Step (3)

The 4-hydroxyl group of Compound (3) is sulfonylated with trifluoromethanesulfonic anhydride to give methyl 3-O-tert-butyldimethylsilyl-2,6-dideoxy-2-fluoro-4-O-trifluoromethylsulfonyl-α-L-talopyranoside [Compound (4)] of the following formula

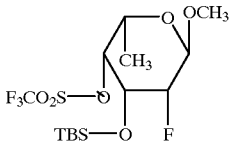

as the 4-O-sulfonylation product.

Step (4)

Compound (4) is reacted with lithium azide in anhydrous N,N-dimethylformamide (DMF), thereby to make the configuration of the 4-position inverted and simultaneously effect the azidation at the 4-position, affording methyl 4-azido-3-O-tert-butyldimethylsilyl-2,4,6-trideoxy-2-fluoro-α-L-mannopyranoside [Compound (5)] of the following formula

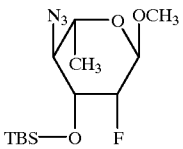

as the 4-azidated product.

Step (5)

The 4-azido group of Compound (5) is converted into 4-amino group by catalytic reduction with hydrogen in the presence of Raney-nickel catalyst, thereby to produce methyl 4-amino-3-O-tert-butyldimethylsilyl-2,4,6-trideoxy-2-fluoro-α-L-mannopyranoside [Compound (6)] of the following formula

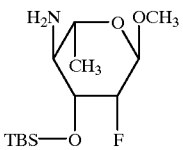

Step (6)

The 4-amino group of Compound (6) is acylated with trifluoroacetic anhydride in pyridine to form methyl 3-O-tert-butyldimethylsilyl-2,4,6-trideoxy-2-fluoro-4-(trifluoroacetylamino)-α-L-mannopyranoside [Compound (7)] having the following formula

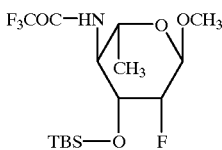

as the 4-N-protected product.

Step (7)

Compound (7) is treated with a mixture of acetic anhydride, acetic acid and sulfuric acid at room temperature, thereby to effect simultaneously the removal of the 3-O-tert-butyldimethylsilyl group, demethylation and di-O-acetylation reactions, affording 1,3-di-O-acetyl-2,4,6-trideoxy-2-fluoro-4-(trifluoroacetylamino)-L- mannopyranose [Compound (8)] having the following formula

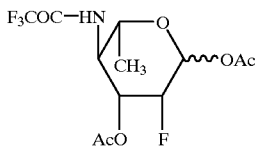

The Compound (8) is a mixture or α-anomer [Compound (8-a)] and β-anomer [Compound (8-b)]. When Compound (8) is subjected to a silica gel column chromatography as developed with dichloromethane, the α-anomer [Compound (8-a)] and the β-anomer [Compound (8-b)] can be isolated from each other.

Step (8)

Compound (8) (ie., the mixture of said α- and β-anomers above) is brominated in a conventional manner in solution of hydrogen bromide in acetic acid, to give 3-O-acetyl-2,4,6-trideoxy-2-fluoro-4-(trifluoroacetylamino)-α-L-mannopyranosyl bromide [Compound (9)] of the following formula

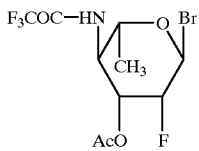

as a 1-bromo-sugar. By the way, the corresponding 1-iodo-sugar can be obtained by reacting Compound (8) with iodo-trimethylsilane in anhydrous toluene.

The above-mentioned Compound (7), Compound (8) and Compound (9) are new compounds.

Similarly to that Compound (9) can be produced from Compound (8) by bromination of the latter as described above, iodination of Compound (8) by an appropriate iodinating agent can produce the corresponding 1-iodo-sugar. Besides, in place of the acetyl group which has protected the 3-hydroxyl group in Compound (9), it is possible to introduce into said 3-hydroxyl group a benzoyl group as another proper hydroxyl-protecting group.

That is to say, when the aforesaid Compound (7) is treated with a mixture of benzoic anhydride, benzoic acid and sulfuric acid, it is feasible to obtain 1,3-di-O-benzoyl-2,4,6-trideoxy-2-fluoro-4-(trifluoroacetylamino)-L-mannopyranose. The latter compound may be brominated by treatment with a solution of hydrogen bromide in acetic acid in a similar way to the aforesaid step (8) to give 3-O-benzoyl-2,4,6-trideoxy-2-fluoro-4-(trifluoroacetylamino)-α-L-mannopyranosyl bromide.

For the preparation of 7-O-(4-amino-2,4,6-trideoxy-2-fluoro-α-L-mannopyranosyl)daunomycinone of formula (Ia) according to the first aspect of this invention, i.e. Compound (a) of this invention, there may be conducted such a process which comprises reacting the 7-hydroxyl group of daunomycinone with the aforesaid bromide compound (9), or generally with a 3,4-di-O,N-protected-4-amino-2,4,6-trideoxy-2-fluoro-α-L-mannopyranosyl halide, for the condensation reaction, followed by removing the hydroxyl-protecting group and/or the amino-protecting group, where remaining, from the resulting condensation product by a conventional method. In this process, it is convenient to adopt such a procedure wherein compound (9) and daunomycinone are dissolved in anhydrous dichloroethane, the resultant solution is then subjected to the condensation reaction in the presence of mercuric bromide or iodide, yellow mercuric oxide and Molecular Sieves 3A, followed by recovering the resulting a-L-condensation product from the reaction solution and then removing the remaining acetyl and trifluoroacetyl groups as the protecting groups by alkaline hydrolysis, thereby to produce Compound (a) of this invention (see Example 2 given hereinafter).

According to a third aspect of this invention, more generally, there is provided a process for the preparation of 7-O-(4-amino-2,4,6-trideoxy-2-fluoro-α-L-mannopyranosyl)daunomycinone represented by the following formula

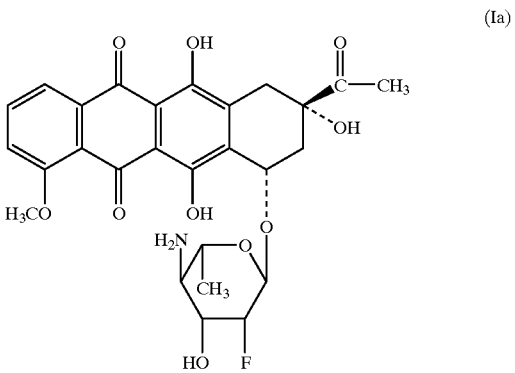

(Ia)

which comprises condensing daunomycinone represented by the following formula

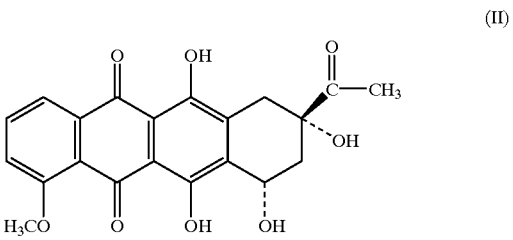

(II)

with a 3,4-di-O,N-protected-4-amino-2,4,6-trideoxy-2-fluoro-L-mannopyranosyl halide represented by the following formula

(III)

wherein Y' is acetyl or benzoyl group as a hydroxyl-protecting group, Y" is trifluoroacetyl group as an amino-protecting group and X is bromine or iodine atom, in an organic solvent in the presence of a condensation catalyst to produce a 7-O-(3,4-di-O,N-protected-4-amino-2,4,6-trideoxy-2-fluoro-α-L-mannopyranosyl)daunomycinone represented by the following formula

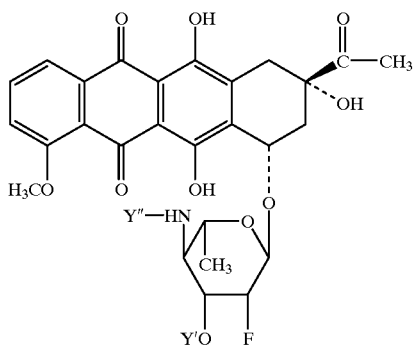

(Ia')

wherein Y' and Y" have the same meanings as defined above, and then removing the remaining hydroxyl-protecting group (Y') and amino-protecting group (Y") from the resulting condensation product of the formula (Ia').

Further, the preparation of 7-O-(4-amino-2,4,6-trideoxy-2-fluoro-α-L-mannopyranosyl)adriamycinone of formula (Ib) according to the first aspect of this invention, i.e. Compound (b) of this invention, may be effected by an application of a known process for converting the 14-methyl group of the daunomycinone derivative of the formula (Ia) into a hydroxymethyl group (refer to Japanese Patent Application first publication Kokai Hei 1-299296 or U.S. Pat. No. 4,125,607).

According to a fourth aspect of this invention, therefore, there is provided, as a process for the preparation of the adriamycinone derivative of formula (Ib) according to the first aspect of this invention, i.e. Compound (b) of this invention, a process for the preparation of 7-O-(4-amino-2,4,6-trideoxy-2-fluoro-α-L-mannopyranosyl)adriamycinone of the formula (Ib), which comprises the steps of reacting 7-O-(4-amino-2,4,6-trideoxy-2-fluoro-α-L-mannopyranosyl)daunomycinone of the formula (Ia) with methyl orthoformate for dimethylketalation of the 13-carbonyl group of the compound of the formula (Ia), thereby to produce a compound having the following formula

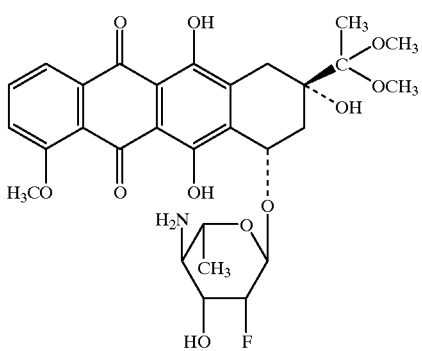

(IV)

and reacting the compound of the formula (IV) with bromine to form a compound having the following formula:

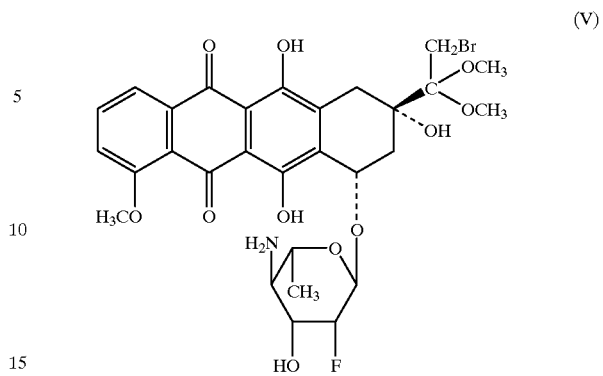

(V)

followed by either hydrolyzing the compound of the formula (V) with hydrobromic acid or subjecting the compound of the formula (V) to a transketalation with acetone, thereby to remove the dimethylketal group therefrom and produce a compound of the following formula

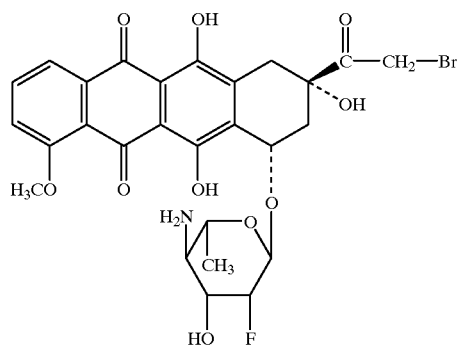

(VI)

and then hydrolyzing the resulting compound of the formula (VI) to convert the group —$CH_2$—Br thereof into a group —$CH_2OH$.

In the above process according to the fourth aspect of this invention for the preparation of the compound of formula (Ib) of this invention, the step for dimethyl-ketalation of the 13-carbonyl group of the daunomycinone derivative of formula (Ia), which is used as starting material, may be carried out by reacting the daunomycinone derivative of formula (Ia) with methyl orthoformate in methanol, dioxane or their mixture at a temperature of 0° C.~50° C. Subsequently, the resulting compound of formula (IV) is reacted with bromine in a halogenated hydrocarbon such as dichloromethane, a lower alkanol such as methanol, or dioxane or tetrahydrofuran at a temperature of 0° C.~50° C. to form the compound of formula (V). For the removal of the dimethylketal group, the compound of formula (V) is then treated with hydrobromic acid or acetone, thereby to give the compound of formula (VI).

The compound of formula (VI) is further reacted with sodium formate or lithium formate to hydrolyze the 14-bromomethyl group (—$CH_2$—Br) into a hydroxymethyl group. The reaction with sodium formate or lithium formate is carried out at 0° C.~50° C. for 1~48 hours in water or a solvent comprising dimethylsulfoxide, dimethylformamide, ethers such as dioxane, tetrahydrofuran, etc. and ketones such as acetone, and the like. If a formyloxy group was occasionally introduced at the 14-position of the so formed adriamycinone derivative as a side reaction occurred, then the decomposition of the formyloxy group may be achieved by subjecting the reaction mixture to a hydrolytic treatment with aqueous ammonia or aqueous sodium hydrogen carbonate (according to a modification of Arcamone's method shown in Example 1 of Japanese Patent Application first publication Kokai Hei 1-299296 or U.S. Pat. No. 4,125,607). Thus, there is afforded the adriamycinone derivative of formula (Ib) according to the first aspect of this invention (refer to Example 3 hereinafter given).

Furthermore, the preparation of the adriamycinone derivative of the formula (Ib) according to the first aspect of this invention may be carried out also by another process which comprises preparing a protected derivative of adriamycinone, namely adriamycinone having the 14-hydroxyl group protected with a suitable hydroxyl-protecting group, preferably triphenylmethyl group (abbreviation: Tr), for example, 14-O-triphenylmethyladriamycinone, and then condensing the 7-hydroxyl group of the 14-O-protected derivative of adriamycinone with Compound (9) mentioned above, generally a 3,4-di-O,N-protected-4-amino-2,4,6-trideoxy-2-fluoro-L-mannopyranosyl halide of the formula (III) shown hereinbefore, and subsequently removing the remaining hydroxyl-protecting group and the remaining amino-protecting group, if remaining, from the resulting condensation product by a conventional method.

According to a fifth aspect of this invention, therefore, there is provided a process for the preparation of 7-O-(4-amino-2,4,6-trideoxy-2-fluoro-α-L-mannopyranosyl) adriamycinone represented by the following formula (Ib)

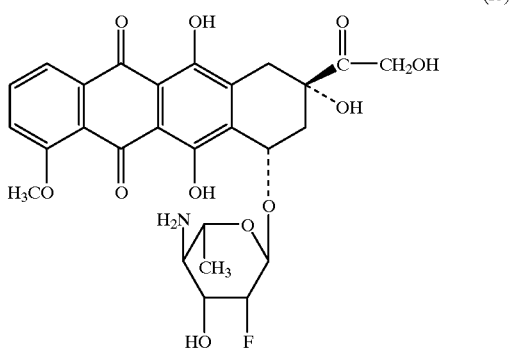

which comprises condensing a 14-O-protected adriamycinone represented by the following formula (VII)

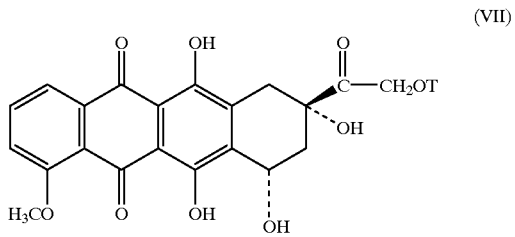

wherein T stands for a hydroxyl-protecting group, with a 3,4-di-O,N-protected-4-amino-2,4,6-trideoxy-2-fluoro-L-mannopyranosyl halide represented by the following formula (III)

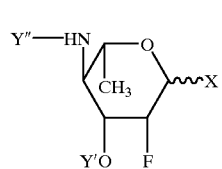

wherein Y' is acetyl or benzoyl group as a hydroxyl-protecting group, Y" is trifluoroacetyl group as an amino-protecting group and X is bromine or iodine atom, in an organic solvent in the presence of a condensation catalyst, to produce a 14-O-protected-7-O-(4-amino-3,4-di-O,N-protected-2,4,6-trideoxy-2-fluoro-α-L-mannopyranosyl) adriamycinone represented by the following formula (Ib')

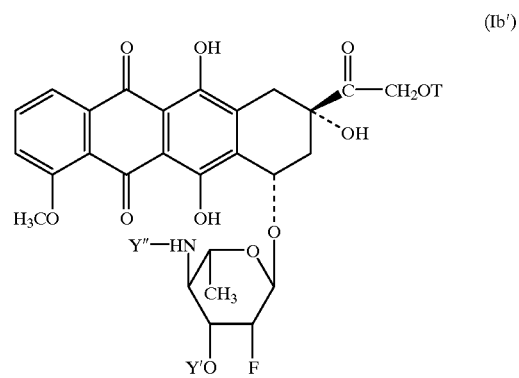

wherein Y', Y" and T have the same meanings as defined above, and removing the remaining hydroxyl-protecting groups (Y' and T) and the remaining amino-protecting group (Y") from the resulting condensation product of the formula (Ib'), if the protecting groups are remaining therein.

The hydroxyl-protecting group (T) in 14-O-protected-adriamycinone of the formula (VII) may preferably be such a group which is easily removable by hydrolysis even under a weakly acidic condition, and which is conveniently triphenylmethyl group but may be p-methoxyphenyldiphenylmethyl group. The protecting group T may be introduced at the 14-hydroxyl group of adriamycinone by a conventional method to give the 14-O-protected derivative of adriamycinone of the formula (VII).

In the process according to the fifth aspect of this invention above-mentioned, it is convenient that the 14-O-protected adriamycinone derivative of the formula (VII) and a mannopyranosyl halide of the formula (III) are dissolved in an organic solvent, e.g. dichloroethane, and the resulting solution is added with mercuric bromide or iodide, yellow mercuric oxide and Molecular Sieves 3A, followed by conducting the desired condensation reaction in the presence of these catalysts. The α-L-condensation product of formula (Ib') thus formed is then recovered from the reaction solution and further subjected to alkaline hydrolysis to eliminate therefrom the remaining acetyl group (or benzoyl group) as the hydroxyl-protecting group Y' and the remaining trifluoroacetyl group as the amino-protecting group Y", and next subjected to acid hydrolysis under a weakly acidic condition to eliminate the remaining 14-O-protecting group (T), e.g. triphenylmethyl group, whereby the target compound (Ib) is produced (see Example 4 hereinafter given).

Further, according to a sixth aspect of this invention, there is provided a use of the daunomycinone or adriamycinone derivative represented by the general formula (I) defined hereinbefore or a pharmaceutically acceptable acid addition salt thereof, in the manufacture of an antitumor composition.

Furthermore, the sugar halide of the general formula (III) shown hereinbefore are new compounds and are useful as intermediates utilizable for the synthesis of the anthracycline derivatives of the general formula (I). Therefore, in a further aspect of this invention, there is provided a 3,4-di-O,N-protected -4-amino-2,4,6-trideoxy-2-fluoro-L-mannopyranosyl halide represented by the following general formula

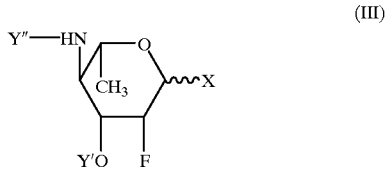

(III)

wherein Y' is acetyl or benzoyl group, Y" is trifluoroacetyl group and X is bromine or iodine atom.

BEST MODE FOR CARRYING OUT THE INVENTION

This invention will now be illustrated more concretely with reference to Example 1 which describes an example of the synthesis of the various 4-amino-2,4,6-trideoxy-2-fluoro-α-L-mannopyranose derivatives, as well as to Examples 2, 3 and 4 which describe examples of the synthesis of the novel anthracycline derivatives of formulae (Ia) and (Ib) according to this invention. In the formulae shown in these Examples 1~4, Bn stands for benzyl group, Ac stands for acetyl group, TBS stands for tert-butyldimethylsilyl group and Tr stands for triphenylmethyl group.

EXAMPLE 1

(1) Preparation of methyl 4-O-benzyl-3-O-tert-butyldimethylsilyl-2,6-dideoxy-2-fluoro-α-L-talopyranoside [Compound (2)]

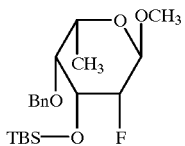

Compound (2)

Methyl 4-O-benzyl-2,6-dideoxy-2-fluoro-α-L-talopyranoside (Compound 1) [described by K. OK, Y. Takagi, T. Tsuchiya, S. Umezawa and H. Umezawa in the "Carbohydrate Research", Vol. 169, pp. 69–81 (1987)] (1.8 g) was dissolved in anhydrous N,N-dimethylformamide (DMF) (3.5 ml). To the resulting solution was added a solution of imidazole (1.24 g) and tert-butylchlorodimethylsilane (1.23 g) in anhydrous DMF (6 ml). The resulting mixture was allowed to stand at room temperature overnight.

To the reaction solution so obtained was added methanol (0.8 ml), and the resulting mixture was then allowed to stand at room temperature overnight. To the resulting reaction solution was added dropwise water. The aqueous mixture so obtained was extracted with chloroform. The chloroform solution (the extract) was washed sucessively with a 10% aqueous solution of potassium hydrogen sulfate, a saturated aqueous solution of sodium hydrogen carbonate and water, then dried over anhydrous sodium sulfate and concentrated under a reduced pressure. The residue obtained was treated repeatedly by adding xylene thereto and concentrating the resulting solution under a reduced pressure, in order to remove DMF. The residue finally obtained was purified by a silica gel column chromatography (development solvent: toluene-ethyl acetate, 25:1), thus affording the titled Compound (2) (2.08 g, yield 86%) as a syrup.

$[\alpha]_D^{26}$ −32° (c 1, chloroform)

$^1$H-NMR spectrum (in deutero-chloroform): δ 3.37 (3H, s, OCH$_3$) 0.95 (9H, s, C(CH$_3$)$_3$) 0.15, 0.14 (each 3H, s, Si(CH$_3$)$_2$)

$^{19}$F-NMR spectrum (in deutero-chloroform, CFCl$_3$, as internal standard): δ −204.3 (ddd)

(2) Preparation of methyl 3-O-tert-butyldimethylsilyl-2,6-dideoxy-2-fluoro-α-L-talopyranoside [Compound (3)]

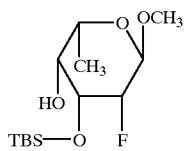

Compound (3)

Compound (2) obtained in step (1) above, namely methyl 4-O-benzyl-3-O-tert-butyldimethylsilyl-2,6-dideoxy-2-fluoro-α-L-talopyranoside, (1.32 g) was dissolved in a mixture of dioxane (40 ml), acetic acid (2.6 ml) and water (4 ml). Into the resulting solution was blown hydrogen gas in the presence of palladium black for 4.5 hours to conduct a catalytic reduction (for the removal of benzyl group). The resulting reaction solution was filtered and the filtrate was concentrated under a reduced pressure. The resulting residue was dissolved in chloroform and the chloroform solution was washed with a saturated aqueous solution of sodium hydrogen carbonate, then dried over anhydrous sodium sulfate and concentrated under a reduced pressure, to afford the titled Compound (3) (0.92 g, 95%) as a syrup.

$[\alpha]_D^{24}$ −84° (c 1, chloroform)

Elemental analysis (for C$_{13}$H$_7$FO$_4$Si) Calculated: C, 53.03; H, 9.24; F, 6.45% Found: C, 53.31; H, 9.57; F, 6.19%

(3) Preparation of methyl 3-O-tert-butyldimethylsilyl-2,6-dideoxy-2-fluoro-4-O-trifluoromethylsulfonyl-α-L-talopyranoside [Compound (4)]

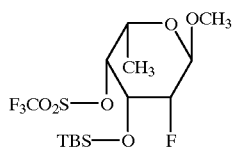

Compound (4)

Compound (2) as obtained in step (2) above, namely methyl 3-O-tert-butyldimethylsilyl-2,6-dideoxy-2-fluoro-α-L-talopyranoside (0.92 g) was dissolved in a mixture of anhydrous dichloromethane (9 ml) and anhydrous pyridine (1.5 ml), and the resulting solution was added with trifluoromethanesulfonic anhydride (0.98 ml) under ice-cooling. The mixture obtained was allowed to stand in an ice bath for 1.5 hours to effect the reaction intended (for the 4-O-trifluoromethylsulfonylation).

To the resulting reaction solution was added methanol (3.8 ml), and the mixture obtained was allowed to stand for 30 minutes and then diluted with chloroform. The resulting chloroform solution was washed successively with a 10% aqueous solution of potassium hydrogen sulfate, an aqueous saturated solution of sodium hydrogen carbonate and water and then dried over anhydrous sodium sulfate. The dried solution was concentrated under a reduced pressure, to afford the titled Compound (4) (1.29 g; 97%) as a solid.

$[\alpha]_D^{23}$ -60° (c 1, chloroform)

$^{19}$F-NMR spectrum (in deutero-chloroform, CFCl$_3$ as internal standard): δ -74.8 (3F, s, CF$_3$) -205.3 (1F, ddd, F-2)

(4) Preparation of methyl 4-azido-3-O-tert-butyldimethylsilyl-2,4,6-trideoxy-2-fluoro-α-L-mannopyranoside [Compound (5)]

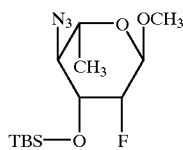

Compound (5)

Compound (4) as obtained in step (3) above, namely methyl 3-O-tert-butyldimethylsilyl-2,6-dideoxy-2-fluoro-4-O-trifluoromethylsulfonyl-α-L-talopyranoside (1.68 g) was dissolved in DMF (17 ml), and the resulting solution was added with lithium azide (0.98 g). The mixture obtained was kept at 90° C. for 1 hour to effect the reaction (for the 4-azidation).

The resulting reaction solution was diluted with chloroform, washed with water, dried over anhydrous sodium sulfate and concentrated under a reduced pressure. The residue obtained was subjected repeatedly to such treatment that xylene was added to the residue and the resulting solution was concentrated under a reduced pressure in order to remove the DMF used. The residue finally obtained was purified by a silica gel column chromatography (development solvent: toluene), to afford the titled Compound (5) (0.75 g; 61%) as a syrup.

$[\alpha]_D^{23}$ -148° (c 1, chloroform)

IR spectrum (KBr disc): 2110 cm$^{-1}$ (N$_3$)

$^1$H-NMR spectrum (in deutero-chloroform): δ 3.34 (1H, t, H-4, $J_{3,4}=J_{4,5}=10$ Hz)

(5) Preparation of methyl 4-amino-3-O-tert-butyldimethylsilyl-2,4,6-trideoxy-2-fluoro-α-L-mannopyranoside [Compound (6)]

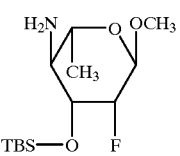

Compound (6)

Compound (5) as obtained in step (4) above, namely methyl 4-azido-3-O-tert-butyldimethylsilyl-2,4,6-trideoxy-2-fluoro-α-L-mannopyranoside (645 mg) was dissolved in dioxane (28 ml). Raney nickel was added to the resulting solution, and the mixture obtained was stirred at room temperature for 1 hour to conduct the reduction reaction (for the reduction of 4-azido group).

The resulting reaction solution was filtered and the filtrate was concentrated under a reduced pressure, to afford the titled Compound (6) (576 mg; yield 97%) as a syrup.

$[\alpha]_D^{23}$ -45° (c 1, chloroform)

Elemental analysis (for C$_{13}$H$_{28}$FNO$_3$Si): Calculated: C, 53.21; H, 9.62; F, 6.47; N, 4.77% Found: C, 53.36; H, 9.64; F, 6.65; N, 4.96%

(6) Preparation of methyl 3-O-tert-butyldimethylsilyl-2,4,6-trideoxy-2-fluoro-4-(trifluoroacetylamino)-α-L-mannopyranoside [Compound (7)]

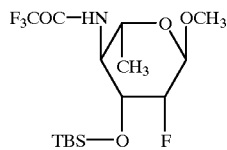

Compound (7)

Compound (6) as obtained in step (5) above, namely methyl 4-amino-3-O-tert-butyldimethylsilyl-2,4,6-trideoxy-2-fluoro-α-L-mannopyranoside (500 mg) was dissolved in a mixture of anhydrous dichloromethane (10 ml) and anhydrous pyridine (1 ml). To the resulting solution was added trifluoroacetic anhydride (0.5 ml) under ice-cooling. The mixture obtained was allowed to stand at room temperature for 2 hours to conduct the reaction (for the trifluoroacetylation of 4-amino group).

Methanol (0.4 ml) was added to the resulting reaction solution under ice-cooling, and the mixture obtained was allowed to stand for 30 minutes for decomposition of any excess of the reagents and then was diluted with chloroform. The chloroform solution obtained was washed successively with a 10% aqueous solution of potassium hydrogen sulfate, an aqueous saturated solution of sodium hydrogen carbonate and water, then dried over anhydrous sodium sulfate and concentrated under a reduced pressure. Thus, the titled Compound (7) (618 mg; 93%) was obtained as a solid.

$[\alpha]_D^{22}$ -50° (c 1, chloroform) $^{19}$F-NMR spectrum (in deutero-chloroform, CFCl$_3$ as internal standard): δ -76.2 (3F, s, CF$_3$) -207.1 (1F, ddd, F-2)

(7) Preparation of 1,3-di-O-acetyl-2,4,6-trideoxy-2-fluoro-4-(trifluoroacetylamino)-L-mannopyranose [Compound (8)]

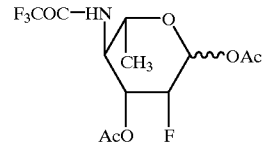

Compound (8)

Compound (7) as obtained in step (6) above, i.e. methyl 3-O-tert-butyldimethylsilyl-2,4,6-trideoxy-2-fluoro-4-(trifluoroacetylamino)-α-L-mannopyranoside (469 mg) was dissolved in a mixture of acetic anhydride (5 ml), acetic acid (5 ml) and sulfuric acid (0.1 ml), followed by effecting the reaction at room temperature for 8 hours (for the 1,3-di-O-acetylation). The resulting reaction solution was poured into a 20% aqueous solution of sodium acetate (110 ml) under ice-cooling, and the mixture obtained was stirred for 1 hour and then extracted with chloroform.

The chloroform solution so obtained was washed successively with an aqueous saturated solution of sodium hydrogen carbonate and water, then dried over anhydrous sodium sulfate and concentrated under a reduced pressure, to afford the titled Compound (8) in the form of a mixture of the α-anomer (Compound 8-a) and the β-anomer (Compound 8-b) (410 mg; yield 99%) as a solid.

$^1$H-NMR spectrum (in deutero-chloroform): δ 2.14, 2.16, 2.20 (6H in combination, each s, OAc)

Elemental analysis (for $C_{12}H_{15}F_4NO_6$): Calculated: C, 41.75; H, 4.38; F, 22.01; N, 4.06% Found: C, 41.95; H, 4.44; F, 22.08; N, 4.11%

(8) Preparation of 3-O-acetyl-2,4,6-trideoxy-2-fluoro-4-(trifluoroacetylamino)-α-L-mannopyranosyl bromide [Compound (9)]

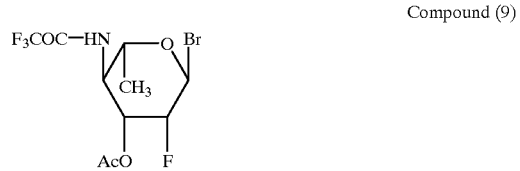

Compound (9)

Compound (8) as obtained in step (7) above, i.e. 1,3-di-O-acetyl-2,4,6-trideoxy-2-fluoro-4-(trifluoroacetylamino)-L-mannopyranose (590 mg) was dissolved in a 30% solution of hydrogen bromide in acetic acid (6 ml). The solution obtained was allowed to stand at room temperature for 2.5 hours to effect the reaction (for the 1-bromination). The resulting reaction solution was diluted with chloroform, and the chloroform solution obtained was washed successively with cold water, a cold aqueous saturated solution of sodium hydrogen carbonate and cold water, then dried over anhydrous magnesium sulfate and concentrated under a reduced pressure. Thus, the titled Compound (9) (549 mg; 88%) was afforded as a syrup.

$^1$H-NMR spectrum: δ 6.45 (1H, dd, H-1) 2.14 (3H, s, OAc)

EXAMPLE 2

(1) Preparation of 7-O-[3-O-acetyl-2,4,6-trideoxy-2-fluoro-4-(trifluoroacetylamino)-α-L-mannopyranosyl]daunomycinone [Compound (10)]

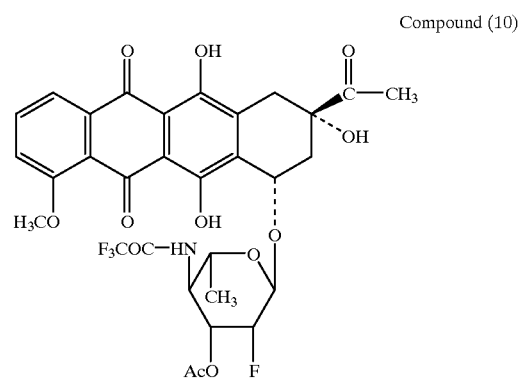

Compound (10)

Daunomycinone (131 mg), yellow mercuric oxide (361 mg), mercuric bromide (123 mg) and powdery Molecular Sieves 3A (1.45 g) were suspended in anhydrous dichloromethane (15 ml), and the resulting suspension was stirred for 30 minutes. Then, to the suspension was added a solution of Compound (9) as obtained in Example 1 (8), namely 3-O-acetyl-2,4,6-trideoxy-2-fluoro-4-(trifluoroacetylamino)-α-L-mannopyranosyl bromide (135 mg) in anhydrous dichloromethane (5 ml). The resulting solution was refluxed in a dark place for 4 hours.

To the reaction solution so obtained were further added yellow mercuric oxide (170 mg) and mercuric bromide (53 mg), and the resultant mixture was further refluxed in a dark place for 24 hours to complete the intended condensation reaction.

The resulting reaction solution was diluted with chloroform and then filtered through Celite. The filtrate was washed successively with a 30% aqueous solution of potassium iodide, an aqueous saturated solution of sodium hydrogen carbonate and water. The washed solution (the filtrate) was dried over anhydrous sodium sulfate and concentrated under a reduced pressure. The resulting residue was subjected to a silica gel column chromatography (development solvent: toluene-acetone, 6:1), for the separation and purification of the target compound. Thus, the titled Compound (10) (111 mg; 60%) was obtained as a red solid.

$[\alpha]_D^{23}$+170° (c 0.06, chloroform)

$^1$H-NMR spectrum (in deutero-chloroform): δ 5.56 (1H, dd, H-1', $J_{1',F}$=7, $J_{1',2}$=2 Hz) 4.06 (3H, s, OCH$_3$) 2.41 (3H, s, Ac) 2.03 (3H, s, OAc)

$^{19}$F-NMR spectrum (in deutero-chloroform, CFCl$_3$ as internal standard): δ −76.5 (3F, s, CF$_3$) −202.8 (1F, ddd, F-2')

(2) Production of 7-O-(4-amino-2,4,6-trideoxy-2-fluoro-α-L-mannopyranosyl)daunomycinone [Compound (11)]

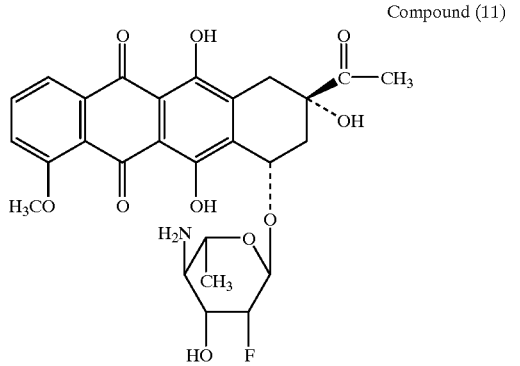

Compound (11)

Aqueous 0.2N sodium hydroxide solution (3.1 ml) was added to Compound (10) as obtained in Example 2 (1) above, namely 7-O-[3-O-acetyl-2,4,6-trideoxy-2-fluoro-4-(trifluoroacetylamino)-α-L-mannopyranosyl] daunomycinone (31 mg). The resulting solution was stirred under an argon atmosphere at 0° C. for 3.5 hours to effect the reaction (for the removal of 3-O-acetyl group and trifluoroacetyl group). After addition of 1N hydrochloric acid (0.7 ml) to the resulting reaction solution, this solution under the acidic condition was washed with chloroform to remove impurities.

To the resulting aqueous solution containing the target Compound (11) was added an aqueous saturated solution of sodium hydrogen carbonate to adjust the pH to 8. Thereafter, the resulting mixture was extracted with chloroform to separate the target Compound (10) therefrom. The chloroform solution obtained was washed with water, dried over anhydrous sodium sulfate and then concentrated under a reduced pressure. The resulting residue was dissolved in a mixture of methanol-chloroform (1:1), and the solution obtained was added with a solution of 0.2N hydrochloric acid in methanol to make the solution acidic and was then added with isopropyl ether to re-precipitate Compound (11). Thus, the titled Compound (11), i.e. Compound (a) of this invention was obtained in the form of hydrochloride (23 mg; yield 87%) as a red solid. The hydrochloride of Compound (a) is dissolved in water at its solubility of 5 mg/ml at 25° C.

$[\alpha]_D^{24}$ +289° (c 0.1, methanol)

$^1$H-NMR spectrum (in deutero-methanol): δ 5.46 (1H, br. d, H-1') 4.01 (3H, s, OCH$_3$) 2.38 (3H, s, Ac)

Elemental analysis (for $C_{27}H_{28}FNO_{10} \cdot HCl \cdot 0.5H_2O$): Calculated: C, 54.87; H, 5.12; F, 3.21; N, 2.37; Cl, 6.00% Found: C, 54.72; H, 5.38; F, 3.05; N, 2.45; Cl 5.81%

EXAMPLE 3

Production of 7-O-(4-amino-2,4,6-trideoxy-2-fluoro-α-L-mannopyranosyl)adriamycinone [Compound (12)]

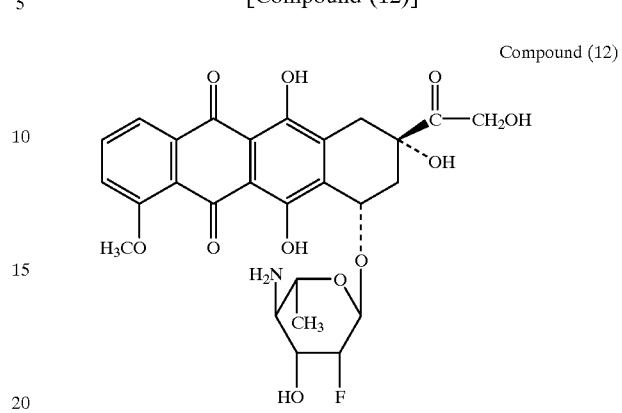

Compound (12)

Compound (11) as obtained in Example 2 (2), namely 7-O-(4-amino-2,4,6-trideoxy-2-fluoro-α-L-mannopyranosyl)daunomycinone (28 mg) was dissolved in a mixture of anhydrous methanol (0.6 ml) and anhydrous dioxane (0.6 ml), and the resulting solution was added with methyl orthoformate (0.032 ml). The mixture obtained was kept at room temperature for 30 minutes to effect the reaction (for the protection of the 13-carbonyl group by dimethylketalation). Then, the resultant reaction solution containing the compound of the formula (IV) formed was cooled to 0° C. and was added with a solution of bromine (11 mg) in anhydrous dichloromethane (0.1 ml). The mixture so obtained was stirred at the temperature of 0° C. for 30 minutes and then further stirred at room temperature for 1 hour, thereby to conduct the bromination at the 14-position of the compound.

To the resulting reaction solution containing the compound of the formula (V) formed were added isopropyl ether (5 ml) and hexane (10 ml) to deposit a red precipitate, which was then separated centrifugally and washed twice with hexane. The precipitate was then suspended in acetone (1.4 ml) and the suspension was stirred at room temperature for 2 hours for effecting the de-ketalation reaction. The resulting reaction solution containing the compound of the formula (VI) produced was added with water (1 ml) and sodium formate (50 mg) and thereafter was stirred at room temperature for 17 hours, to give a reaction solution containing Compound (12) as formed and by-products. In order to recover Compound (12), this reaction solution was diluted with water and concentrated under a reduced pressure to eliminate acetone present therein. The remaining aqueous solution was washed with chloroform. The chloroform solution obtained was washed twice with water, and the resultant washings were combined with said remaining aqueous solution.

The said aqueous solution was then added with sodium hydrogen carbonate (3 g) and sodium chloride (350 mg) and then was extracted with chloroform. The chloroform solution so obtained was washed with water, dried over anhydrous sodium sulfate and concentrated under a reduced pressure. The resulting residue was dissolved in a mixture of methanol (0.5 ml) and chloroform (0.5 ml), and to the resultant solution was added a solution of 2N hydrochloric acid in methanol (0.13 ml) to effect the reaction of addition of hydrochloric acid to the amino group of Compound (12).

Subsequently, isopropyl ether was added to the resulting reaction solution to cause deposition of a precipitate, which was then recovered by centrifugation. Thereby, the titled Compound (12), i.e. Compound (b) of this invention was obtained in the form of hydrochloride (17 mg; 61%) as a red solid. The hydrochloride of Compound (b) is dissolved in water at a solubility of 6 mg/ml at 25° C.

$[\alpha]_D^{21}$ +285° (c 0.1, methanol)

$^1$H-NMR spectrum (in deutero-water, 45° C.): δ 5.45 (1H, br. d, H-1') 4.82 (2H, AB q, H-14a, 14b) 3.81 (3H, s, OCH$_3$)

$^{19}$F-NMR-spectrum (in deutero-water, CFCl$_3$ as internal standard): δ −206.4 (br. dd, F-2')

EXAMPLE 4

(1) Preparation of 7-O-[3-O-acetyl-2,4,6-trideoxy-2-fluoro-4-(trifluoroacetylamino)-α-L-mannopyranosyl]-14-O-triphenylmethyladriamycinone [Compound (13)]

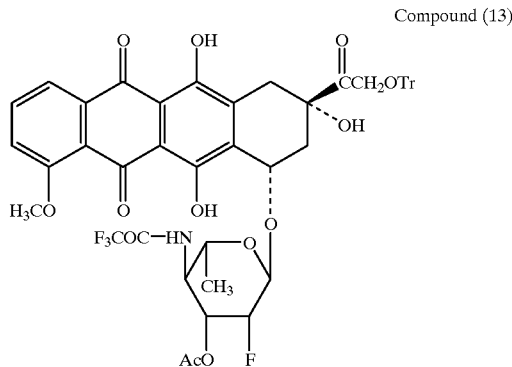

14-O-Triphenylmethyladriamycinone (215 mg), yellow mercuric oxide (568 mg), mercuric bromide (236 mg) and powdery Molecular Sieves 3A (600 mg) were suspended in anhydrous dichloromethane (6 ml), and the resulting suspension was stirred for 30 minutes. Subsequently, to the suspension was added a solution of Compound (9) as obtained in Example 1 (8), namely 3-O-acetyl-2,4,6-trideoxy-2-fluoro-4-(trifluoroacetylamino)-α-L-mannopyranosyl bromide (120 mg) in anhydrous dichloromethane (2 ml). The mixture obtained was refluxed in a dark place for 19 hours to conduct the condensation reaction intended.

The reaction solution so formed was diluted with chloroform and filtered through Celite, and the filtrate was washed successively with a 30% aqueous solultion of potassium iodide, an aqueous saturated solution of sodium hydrogen carbonate solution and water. The chloroform solution thus washed was dried over anhydrous sodium sulfate and concentrated under a reduced pressure. The resulting residue was subjected to a silica gel column chromatography (development solvent: toluene-acetone, 12:1), for the separation and purification of the target compound. The titled Compound (13) (157 mg; 51%) was afforded as a red solid.

$[\alpha]_D^{24}$ +137° (c 0.2, chloroform)

$^1$H-NMR spectrum (in deutero-chloroform): δ 5.48 (1H, dd, H-1') 4.06 (3H, s, OCH$_3$) 2.02 (3H, s, OAc)

(2) Production of 7-O-(4-amino-2,4,6-trideoxy-2-fluoro-α-L-mannopyranosyl)adriamycinone [Compound (12)]

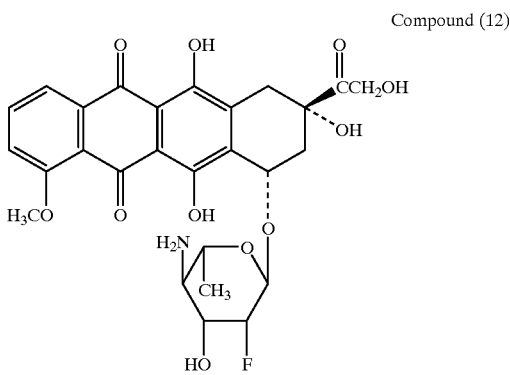

Compound (13) as obtained in Example 4 (1), namely 7-O-[3-O-acetyl-2,4,6-trideoxy-2-fluoro-4-(trifluoroacetylamino)-α-L-mannopyranosyl-14-O-triphenylmethyladriamycinone (52 mg) was dissolved in a 0.2N solution of sodium hydroxide in chloroform-methanol (2:1) (5 ml). The solution obtained was stirred under an argon atmosphere at 0° C. for 1 hour and then at room temperature for 3 hours to effect the reaction (for the removal of both the 3-O-acetyl group and trifluoroacetyl group). The resultant reaction solution was neutralized by adding a small piece of Dry Ice and then diluted with water and extracted with chloroform to separate the desired compound. The chloroform solution obtained was concentrated under a reduced pressure, and the residue was dissolved in a 80% aqueous solution of acetic acid (3 ml). The resulting solution was heated at 80° C. under the weakly acidic condition for 2 hours (for the elimination of triphenylmethyl group).

The resulting reaction solution was concentrated, and the residue was added to xylene. The resulting mixture was subjected repeatedly to concentration under a reduced pressure to remove the acetic acid. The residue so obtained was washed with ethyl ether. The resulting solid-was dissolved in water and the aqueous solution was charged into a column packed with Diaion HP-20 resin (30 ml). The resin column was then developed with solvents which were gradually varying from water to methanol. Among the eluates, such fractions containing Compound (12) were concentrated under a reduced pressure. The resulting residue was re-precipitated in the same manner as in Example 3, to give the titled Compound (12), i.e. Compound (b) of this invention in the form of hydrochloride (20 mg; 61%) as a red solid. This compound corresponded to the Compound (12) as obtained in Example 3 in respect of its physical properties and spectral data.

INDUSTRIAL APPLICABILITY

The anthracycline derivatives of the general formula (I) provided by this invention have remarkably excellent anticancer or antitumor activities and are soluble in water. It is expected that the novel compounds according to this invention are useful as an anticancer or antitumor agent.

We claim:

1. A 3,4-di-O,N-protected-4-amino-2,4,6-trideoxy-2-fluoro-L-mannopyranosyl halide represented by the following formula

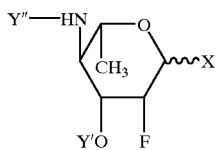
(III)

wherein Y' is acetyl or benzoyl group, Y" is trifluoroacetyl group and X is bromine or iodine atom.

2. A process of preparing a 3,4-di-O,N-protected-4-amino-2,4,6-trideoxy-2-fluoro-L-mannopyranosyl halide of the formula (III)

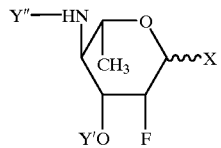
(III)

wherein Y' is acetyl or benzoyl group, Y" is trifluoroacetyl group and X is bromine or iodine atom, which comprises consecutive steps of reacting the 3-hydroxyl group of methyl 4-O-benzyl-2,6-dideoxy-2-fluoro-α-L-talopyranoside (Compound (1)) of the formula

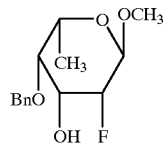

wherein Bn denotes benzyl group, with tert-butylchlorodimethylsilane to produce methyl 4-O-benzyl-3-O-tert-butyldimethylsilyl-2,6-dideoxy-2-fluoro-α-L-talopyranoside (Compound (2)) of the formula

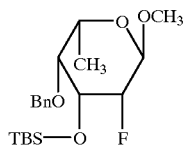

wherein Bn is as defined above and TBS denotes tert-butyldimethylsilyl group, eliminating the benzyl group at the 4-position of compound (2) therefrom by catalytic reduction with hydrogen in the presence of a palladium catalyst, to produce methyl 3-O-tert-butyldimethylsilyl-2,6-dideoxy-2-fluoro-α-L-talopyranoside (Compound (3)) of the formula

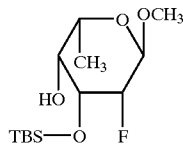

wherein TBS is as defined above, sulfonating the 4-hydroxyl group of Compound (3) with trifluoromethanesulfonic anhydride to produce methyl 3-O-tert-butyldimethylsilyl-2,6-dideoxy-2-fluoro-4-O-trifluoromethylsulfonyl-α-L-talopyranoside (Compound (4)) of the formula

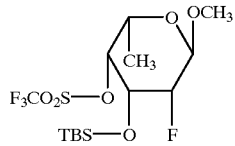

wherein TBS is as defined above, as the 4-O-sulfonylation product, reacting this Compound (4) with lithium azide in anhydrous N,N-dimethylformamide, to make the configuration of the 4-position inverted and simultaneously effect the azidation at the 4-position and thus to afford methyl 4-azido-3-O-tert-butyldimethylsilyl-2,4,6-trideoxy-2-fluoro-α-L-mannopyranoside (Compound (5)) of the formula

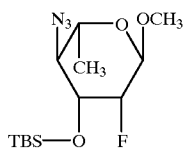

wherein TBS is as defined above, as the 4-azidated product, reducing the 4-azido group of Compound (5) into 4-amino group by catalytic reduction with hydrogen in the presence of Raney-nickel catalyst, to produce methyl 4-amino-3-O-tert-butyldimethylsilyl-2,4,6-trideoxy-2-fluoro-α-L-mannopyranoside (Compound (6)) of the formula

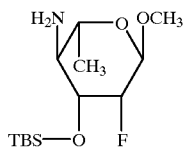

wherein TBS is as defined above, acylating the 4-amino group of Compound (6) with trifluoroacetic anhydride in pyridine, to form methyl 3-O-tert-butyldimethylsilyl-2,4,6-trideoxy-2-fluoro-4-(trifluoroacetylamino)-α-L-mannopyranoside (Compound (7)) of the formula

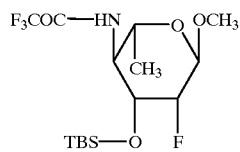

wherein TBS is as defined above, as the 4-N-protected product, treating this Compound (7) with a mixture of acetic anhydride, acetic acid and sulfuric acid at room temperature, to effect simultaneously the removal of the 3-O-tert-butyldimethylsilyl group, demethylation and di-O-acetylation reactions, and thus to afford 1,3-di-O-acetyl-2,4,6-trideoxy-2-fluoro-4-(trifluoroacetylamino)-L-mannopyranose (Compound (8)) of the formula

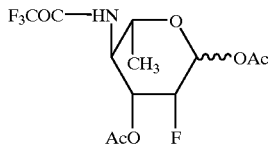

wherein Ac denotes acetyl group, or treating the aforesaid Compound (7) with a mixture of benzoic anhydride, benzoic acid and sulfuric acid, to obtain 1,3-di-O-benzoyl-2,4,6-trideoxy-2-fluoro-4-(trifluoroacetylamino)-L-mannopyranose Compound (8'), and then brominating Compound (8) or Compound (8') in a solution of hydrogen bromide in acetic acid, or iodinating Compound (8) or Compound (8') with iodotrimethylsilane in anhydrous toluene to give 3-O-acetyl or benzoyl-2,4,6-trideoxy-2-fluoro-4-(trifluoroacetylamino)-α-L-mannopyranosyl bromide or iodide of the formula (III) above or represented by the following formula (III')

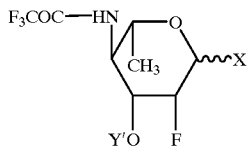

(III')

wherein Y' is acetyl or benzoyl group and X is bromine or iodine atom.

3. Methyl 4-amino-3-O-tert-butyldimethylsilyl-2,4,6-trideoxy-2-fluoro-α-L-mannopyranoside (Compound (6)) of the formula

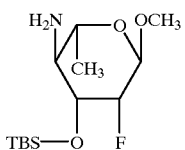

wherein TBS denotes tert-butyldimethylsilyl group.

* * * * *